United States Patent [19]

Räder et al.

[11] 4,362,730

[45] Dec. 7, 1982

[54] VINCAMINE SACCHARINATE AND A PHARMACEUTICAL COMPOSITION CONTAINING IT DISSOLVED THEREIN

[75] Inventors: Kurt Räder, Ochsenhausen; Peter Stoss, Illertissen, both of Fed. Rep. of Germany

[73] Assignee: Heinrich Mack Nachf. Chem-Pharm. Fabrik, Illertissen, Fed. Rep. of Germany

[21] Appl. No.: 283,706

[22] Filed: Jul. 16, 1981

[30] Foreign Application Priority Data

Aug. 25, 1980 [DE] Fed. Rep. of Germany ....... 3031953

[51] Int. Cl.³ .................. A61K 31/435; C07D 461/00
[52] U.S. Cl. ........................................ 424/256; 546/51
[58] Field of Search .......................... 424/256; 546/51; 548/211

[56] References Cited

U.S. PATENT DOCUMENTS 2,134,714 11/1938 Glassman ........................ 548/211 X
2,538,645 1/1951 Hamilton ........................ 548/211 X
4,122,179 10/1978 Vegezzi .............................. 424/180

FOREIGN PATENT DOCUMENTS 2604044 3/1976 Fed. Rep. of Germany .
2725246 3/1977 Fed. Rep. of Germany .
2832587 2/1979 Fed. Rep. of Germany .
2193586 7/1972 France .
2193587 7/1972 France .
2294325 9/1975 France .

OTHER PUBLICATIONS

Brookes, L. G., "Use of Synthetic Sweetening Agents", Chemist Druggist, 183 (4445), 421, (1965).
Dictionaire Vidal, (1978), p. 1545.

*Primary Examiner*—Donald G. Daus
*Assistant Examiner*—Diana G. Rivers
*Attorney, Agent, or Firm*—Charles J. Knuth; Peter C. Richardson; Allen Bloom

[57] ABSTRACT

Vincamine saccharinate, a novel derivative of vincamine, and pharmaceutical compositions containing vincamine saccharinate are disclosed. The solubility of vincamine saccharinate in glycerol-ethanol mixtures and the superior taste characteristics of vincamine saccharinate allow the preparation of preferred pharmaceutical compositions in solution form which are suitable for oral administration, especially in the form of drops.

4 Claims, No Drawings

VINCAMINE SACCHARINATE AND A PHARMACEUTICAL COMPOSITION CONTAINING IT DISSOLVED THEREIN

BACKGROUND OF THE INVENTION

The present invention relates to a novel vincamine derivative, namely vincamine saccharinate, and to pharmaceutical compositions containing this novel compound.

Vincamine is an alkaloid, isolated from *Vinca minor L.*, which is well known to have pharmacological activity as a vasodilator and has been used for the treatment of cerebral circulatory and neurological disorders. Vincamine base is substantially insoluble in water and other pharmaceutically acceptable solvents and has been primarily administered orally in solid dosage forms, such as tablets or dragees. Vincamine has also been available, as the chlorohydrate salt, in solid form in ampoules for the preparation, by reconstitution with water, of dilute aqueous solutions, less than about 0.5% w/w, or suspensions, suitable for administration by injection.

A particular problem has been to find a form of vincamine, as a salt or other derivative, which is sufficiently soluble in a pharmaceutically acceptable solvent to provide a sufficient concentration of the drug in solution such that administration in solution form, preferably as drops, is possible, i.e. to provide the necessary dosage amount of the drug in an acceptably small volume of the solvent. In this regard, a further most significant problem has been that even the few salts or complexes of vincamine which have been found to be relatively soluble in pharmaceutically acceptable solvents, for example vincamine citrate or tartrate in glycerol-ethanol mixtures, and which would therefore provide an adequate concentration of the drug in solution, have an extremely bitter and unpleasant taste which has been impossible to mask or overcome by, for example, the addition of flavoring agents. The failure to find a form of vincamine that has both the desired solubility and acceptable taste characteristics has heretofore precluded the development of medicinally acceptable liquid pharmaceutical compositions for oral administration, especially of solutions having a sufficient concentration of the active drug that can be administered as drops. Accordingly, there has been a substantial need for a derivative of vincamine which provides relatively high solubility in a pharmaceutically acceptable solvent, but which does not have bitter or otherwise unpleasant taste characteristics.

SUMMARY OF THE INVENTION

It has now been found that the novel compound vincamine saccharinate is sufficiently soluble in glycerol-ethanol mixtures to provide adequate concentrations of the active ingredient in solution and at the same time its taste characteristics are acceptable for liquid pharmaceutical compositions suitable for oral administration. Accordingly, the present invention comprises the novel compound vincamine saccharinate and also embraces pharmaceutical compositions of vincamine saccharinate and a pharmaceutically acceptable diluent or carrier. In particular, pharmaceutical compositions included in the present invention comprise from about 0.5 to 3% (w/w) of vincamine saccharinate dissolved in a solvent consisting of about 10 to 90 parts by weight of glycerol and about 90 to 10 parts by weight of ethanol. A particularly preferred pharmaceutical composition comprises about 3% (w/w) vincamine saccharinate dissolved in a mixture of about 70 parts by weight of glycerol and about 30 parts by weight of ethanol.

DETAILED DESCRIPTION OF THE INVENTION

The novel compound of this invention, vincamine saccharinate, is prepared by reaction of vincamine base and saccharin (1,2-benzisothiazol-3(2H)-one-1,1-dioxide). The reaction may be effected by dissolving vincamine base in an acid, such as hydrochloric acid, sulfuric acid, phosphoric acid, lactic acid, citric acid, ketoglutaric acid, maleic acid, malonic acid, tartaric acid or the like, followed by the addition of an equimolar amount of a saccharinate salt in aqueous solution, preferably an alkali metal saccharinate such as sodium or potassium saccharinate. Vincamine saccharinate is formed as a precipitate and can be readily separated, for example by filtration, and, if desired, purified, for example, by redissolving the vincamine saccharinate by heating the precipitate in acetone under reflux, followed by concentration of the solution and the addition of water, whereupon the vincamine saccharinate reprecipitates.

In an alternative procedure, vincamine base and saccharine may be added to a lower alkyl alcohol, preferably methanol, followed by the addition of water and heating to a temperature of about 50° C. to about 55° C. On cooling, for example to about 0° C., vincamine saccharinate is obtained as a crystalline solid.

The vincamine saccharinate, formed as described above, has a melting point, with decomposition, in the range 189° C. to 194° C., depending on the initial temperature and heating rate employed in measuring the melting point.

While not wishing to be bound by any particular statement or theory as to the nature of the product formed, as described hereinabove, it is believed that vincamine saccharinate is in fact a salt. The vincamine saccharinate obtained as described above is believed to be in a hydrated form, the water content being in the range of 0.5 moles to 1.0 mole of water per mole of vincamine saccharinate. If desired, anhydrous vincamine saccharinate may be obtained by, for example, heating the hydrated form to about 50° C. under high vacuum. However, the anhydrous compound is hygroscopic and will, on exposure to the atmosphere, revert to the hydrated form. The term vincamine saccharinate as used in the specification and claims hereof is meant to embrace the product formed by combination of equimolar amounts of vincamine or its salts with saccharine or saccharinates, regardless of the precise physical nature or structure of the product.

Vincamine saccharinate is useful as a vasodilator for treatment of cerebral circulatory conditions, such as cerebral hypoxia, and neurological disorders associated therewith, such as aphasia, apraxia and agnosia, in warm blooded animals, especially in humans. The vincamine saccharinate is generally administered orally in doses of between about 0.8 to 1.3 mg/kg/day, preferably about 1 mg/kg/day, either in a single dose or, preferably, from two to four doses per day. Such dosage amounts are significantly below the $LD_{50}$ values determined for vincamine saccharinate in mice, namely, 2900 mg/kg p.o. and 560 mg/kg i.p.

While vincamine saccharinate may, if desired, be administered orally in the form of solid pharmaceutical compositions comprising vincamine saccharinate and a pharmaceutically acceptable solid carrier or filler, in dosage forms such as tablets, capsules, dragees or powders, the solubility and taste characteristics of vincamine saccharinate make it particularly suitable for administration in liquid pharmaceutical compositions. In particular, pharmaceutical compositions comprising from about 0.5 to 3% (w/w), preferably from about 2 to 3%, most preferably about 3%, of vincamine saccharinate dissolved in a solvent mixture of about 10 to 90 parts by weight of glycerol and 90 to 10 parts by weight of ethanol, especially 70 parts of glycerol and 30 parts of ethanol, are preferred, since such solutions contain a sufficient concentration of the active ingredient in solution so as to provide the necessary dosage amount of the drug in a limited volume of liquid and are thus readily administered orally, especially in the form of drops. Thus, for example, administration of between about 0.5 to 1 ml of a solution containing between about 2 and 3% (w/w) provides the necessary dosage amount of active ingredient when administered orally in from 2 to 4 doses per day.

Ethanol for use in the solvent mixture of the pharmaceutical compositions described above may be commercial grade ethanol, i.e. 92.3% w/w of ethanol, the remainder being water, but is preferably absolute (99.9% w/w) ethanol. Glycerol for use in the present invention may be 85% w/w glycerol, the remainder being water, but is preferably anhydrous glycerol.

If desired, additional conventional ingredients, such as coloring matter or dyes, preservatives, flavoring agents and the like may be added to the above described pharmaceutical compositions in solution form.

In addition to the pharmaceutical compositions in solution form previously described, pharmaceutical compositions in liquid form comprising suspensions of vincamine saccharinate in a pharmaceutically acceptable liquid medium are also of value for oral administration, because of the superior taste characteristics of vincamine saccharinate. Such suspensions may contain from about 0.5 to 10% (w/w) of vincamine saccharinate in an aqueous or organic medium, for example in aqueous sorbitol solutions, together with, if desired, additional ingredients such as flavoring agents, emulsifying or dispersing agents, coloring matter or dyes, preservatives and the like.

The present invention is illustrated by the following examples. However, it should be understood that the invention is not limited to the specific details of these examples.

EXAMPLE 1

0.1 mol of vincamine base (35.44 g) and 0.1 mol of tartaric acid (15.0 g) are dissolved in 1.75 l water. Immediately after dissolution of the mixture 0.1 mol sodium saccharinate (20.5 g) dissolved in 100 ml water is added under stirring at room temperature. After one hour of stirring the precipitate is filtered off and heated under reflux in acetone.

The filtered solution is concentrated by evaporation to about 100 ml and then 700 ml of water is added. After standing for 24 hours in a refrigerator the precipitate is filtered off and dried to yield vincamine saccharinate m.p. 189.4° C. (yield(after rework of the mother liquor) 50.8 g=95%).

EXAMPLE 2

3.0 l methanol, 354.4 g vincamine and 183.2 g saccharine are placed into a 6.0 l flask equipped with stirrer and thermometer. Whilst stirring, 300 ml deionized water are added and the contents heated up to 50°–55° C. A clear solution results, which is filtered and cooled down to 0° C. under further stirring. The crystalline product is then filtered off and washed with a cold (0° C.) solution of 0.5 l methanol plus 50 ml deionized water. The product is dried in an oven at 40° C. under water pump vacuum. Yield: 490 g vincamine saccharinate Melting point: 192° C. (with decomposition) (melting point apparatus type Buchi 510, initial temperature 180° C., heating rate 2° C./min.)
Elemental Analysis:
Found: C, 60.86; H, 5.84; N, 7.68; S, 5.71. Calculated for $C_{28}H_{31}N_3O_6S.1/2H_2O$: C, 61.52; H, 5.90; N, 7.68; S, 5.86.
Calculated for $C_{28}H_{31}N_3O_6S.H_2O$: C, 60.52; H, 5.98; N, 7.56; S, 5.77.

The anhydrous form of vincamine saccharinate is formed by heating the product of the Example to 50° C. under high vacuum.
Elemental analysis:
Found: C, 62.39; H, 5.90; N, 7.71. Calculated for $C_{28}H_{31}N_3O_6S$: C, 62.55; H, 5.81; N, 7.81.

EXAMPLE 3

Vincamine saccharinate 3.0 g is dissolved under stirring at room temperature in 97 g of mixture consisting of 70 parts (by weight) Glycerol "Europaisches Arzneibuch III" 85% w/w and 30 parts (by weight) of Ethanol 99.9%. After about 4 hours the solution is filtered. The resulting solution is suitable for oral administration in the form of drops.

EXAMPLE 4

Parahydroxybenzoic acid methyl ester (0.21 g) and parahydroxybenzoic acid propyl ester (0.09 g) were dissolved by heating in 35 g water and mixed with 35 g of a 70% by weight aqueous solution of sorbitol. Vincamine saccharinate (9.085 g) was suspended in this mixture and "POLYSORBAT 60" (0.05 g) was added. The suspension was adjusted to a pH between 6.5 and 7.5 by the addition of sodium bicarbonate solution and diluted with water to 100 g to provide a pharmaceutical composition in suspension form suitable for oral administration.

We claim:
1. Vincamine saccharinate.
2. Vincamine saccharinate in a pharmaceutically acceptable carrier or diluent.
3. A pharmaceutical composition comprising 0.5 to 3% (w/w) of vincamine saccharinate dissolved in a solvent consisting of from 10 to 90 parts by weight of glycerol and from 90 to 10 parts by weight of anhydrous ethanol.
4. A pharmaceutical composition comprising about 3% (w/w) vincamine saccharinate dissolved in a solvent consisting of about 70 parts of glycerol and about 30 parts of ethanol.

* * * * *